(12) United States Patent
Hemphill et al.

(10) Patent No.: US 11,763,997 B2
(45) Date of Patent: Sep. 19, 2023

(54) ELECTROLYTIC CAPACITOR

(71) Applicant: Pacesetter, Inc., Sylmar, CA (US)

(72) Inventors: R. Jason Hemphill, Sunset, SC (US); A. Corina Geiculescu, Easley, SC (US)

(73) Assignee: Pacesetter, Inc., Sylmar, CA (US)

( * ) Notice: Subject to any disclaimer, the term of this patent is extended or adjusted under 35 U.S.C. 154(b) by 68 days.

(21) Appl. No.: 17/315,493

(22) Filed: May 10, 2021

(65) Prior Publication Data
US 2022/0359126 A1 Nov. 10, 2022

(51) Int. Cl.
*H01G 9/00* (2006.01)
*A61N 1/39* (2006.01)
*H01G 9/028* (2006.01)

(52) U.S. Cl.
CPC ......... *H01G 9/0029* (2013.01); *A61N 1/3956* (2013.01); *H01G 9/028* (2013.01)

(58) Field of Classification Search
CPC ..... H01G 9/0029; H01G 9/028; A61N 1/3956
See application file for complete search history.

(56) References Cited

U.S. PATENT DOCUMENTS

| | | | | |
|---|---|---|---|---|
| 6,587,329 B1 * | 7/2003 | Feger | ...................... | H01G 9/022 361/523 |
| 6,743,370 B1 * | 6/2004 | Feger | ...................... | H01G 9/035 252/62.2 |
| 6,744,619 B1 * | 6/2004 | Feger | ...................... | H01G 9/145 29/25.03 |
| 7,196,899 B1 * | 3/2007 | Feger | ...................... | H01G 9/14 29/25.03 |
| 7,268,996 B1 * | 9/2007 | Dapo | ...................... | H01G 9/035 361/519 |
| 7,585,428 B1 * | 9/2009 | Marshall | ...................... | H01G 9/035 252/62.2 |
| 7,715,174 B1 * | 5/2010 | Beauvais | ...................... | H01G 9/048 361/519 |
| 7,952,853 B2 * | 5/2011 | Viste | ...................... | C25D 11/02 361/504 |
| 8,675,348 B2 * | 3/2014 | Viste | ...................... | C25D 11/12 361/523 |
| 9,105,401 B2 * | 8/2015 | Dreissig | ...................... | H01G 9/035 |
| 9,111,685 B2 * | 8/2015 | Kawakami | ...................... | H01G 9/035 |
| 2002/0067589 A1 * | 6/2002 | Marshall | ...................... | H01G 9/022 361/503 |
| 2022/0359126 A1 * | 11/2022 | Hemphill | ...................... | H01G 9/0029 |

FOREIGN PATENT DOCUMENTS

| | | | | |
|---|---|---|---|---|
| CN | 105575665 A | * | 5/2016 | |
| CN | 108766768 A | * | 11/2018 | ............. H01G 9/028 |
| CN | 110010354 A | * | 7/2019 | ........... H01G 9/0029 |
| CN | 113611535 A | * | 11/2021 | |

* cited by examiner

*Primary Examiner* — Dion R. Ferguson
(74) *Attorney, Agent, or Firm* — THE SMALL PATENT LAW GROUP LLC; Dean D. Small (57) ABSTRACT

A method is provided for manufacturing an electrolytic capacitor for an implantable cardioverter defibrillator. The method includes forming an ester material by adding at least one acid to a glycol, and quenching the ester material for a determined period. The method also includes adding an ammonium based material to the ester material after the ester material is quenched, and adding an additional acid after adding the ammonium based material to form an electrolytic material for the electrolytic capacitor.

20 Claims, 3 Drawing Sheets

ELECTROLYTIC CAPACITOR

BACKGROUND

Embodiments herein generally relate to electrolytic capacitors utilized for implanted medical devices (IMDs).

High voltage capacitors are utilized as energy storage reservoirs in many applications, including IMDs. These capacitors are required to have a high energy density, to minimize the overall size of the implanted device. Further, for IMD applications, because the IMD is subcutaneous, or under the skin of the patient, the size of the IMD must remain minimal. Meanwhile, the capacitor can represent the largest electrical component within the IMD. In one example the IMD can be an implantable cardioverter defibrillator (ICD), or more specifically a subcutaneous implantable cardioverter defibrillator (SICD), High voltage ventricular-tachy therapies are delivered by subcutaneous implantable cardioverter defibrillator (SICD) devices after the tachycardia episode is detected and classified. Currently marketed SICD devices use a conventional bi-phasic capacitive discharge waveform that is delivered from a bank of multiple capacitors that are connected in series. Conventional SICD devices deliver about 80 joules of energy in a single bi-phasic shock. In order to generate a high energy shock of 80 J, conventional SICD devices require a bank of large high voltage capacitors connected in series and typically charged to 800V-900V. The capacitor bank and battery are two of the larger components in SICD devices and thus the overall size of the device is largely dependent on the space needed to house the capacitor bank and battery. For example, the space requirements of the capacitor bank and battery cause the SICD devices to be 60 cc, 70 cc or larger.

One type of high voltage capacitor is an aluminum electrolytic capacitor. Aluminum electrolytic capacitors energy density is directly related to the surface area of the anodes generated in the electrochemical etching processes. However, the electrolyte that is used for the ionic mobility of the charge through from the anode to the cathode is important for the efficiency of the discharge (e.g. delivered to store ratio—DSR). The need is for the delivered energy within 10 to 15 milliseconds to be as close as possible to the stored energy applied from the battery. Higher conductivity electrolytes help reduce the resistance of the discharge to increase the efficiency by improving DSR. However, as the working voltage increases for the capacitor use, scintillations can occur that can lead to damage to the oxide in use or during the aging process, resulting in growing oxide on the edges of the foil after stamping or laser cutting. The damage can lead to loss of energy in those areas or could prevent full voltage/energy discharge.

With the need of the SICD capacitor pair be a 50 J output at higher voltages of 925 Volts and maintain higher than 6 J/cc, the optimization of conductivity per working voltage while keeping the scintillations low is even more difficult without lowering significant efficiency in the delivered to store energy ratio via lower conductivity.

SUMMARY

In accordance with embodiments herein, a method is provided for manufacturing an electrolytic capacitor for an implantable cardioverter defibrillator. The method includes forming an ester material by adding at least one acid to a glycol, and quenching the ester material for a determined period. The method also includes adding an ammonium based material to the ester material after the ester material is quenched, and adding an additional acid after adding the ammonium based material to form an electrolytic material for the electrolytic capacitor.

Optionally, forming an ester material includes heating the at least one acid and glycol to between 120° C.-130° C. for 25-35 minutes to provide esterification. In one aspect, the at least one acid includes azelaic acid and boric acid, and the glycol is ethylene glycol. In another aspect, the ammonium based material is not added to the at least one acid and glycol when forming the ester material. In one example, the ammonium based material is at least one of ammonium hydroxide or anhydrous ammonia. In another example, the quenching the ester material includes cooling the ester material to between 55° C.-65° C. during the determined period. Optionally, the determined period is between 25-35 minutes. In yet another aspect, the additional acid is phosphoric acid.

In accordance with embodiments herein, an electrolytic capacitor for an implantable cardioverter defibrillator is provided. The electrolytic capacitor includes, an electrolytic material having a conductivity between 2.3 to 2.9 mS/cm at between 29° C. to 31° C. and a scintillation rate of between 0.4% and 2%.

Optionally, the electrolytic material has a pH in a range between 6.8 to 7.4. In one aspect, the electrolytic material has a moisture content in a range between 1.0-2.4%. In another aspect, the electrolytic material has a phosphate concentration in a range between 125 to 225 ppm. In one example, the electrolytic material has a deformation rate of between 2% and 5% after one year. In one example, the electrolytic material has a deformation rate of less than 20% after 6 years. In another example, the electrolytic material has a delivered to store ratio (DSR) of greater than 0.9. Alternatively, the electrolytic material has a delivered to store ratio of between 0.88 and 0.93.

In accordance with embodiments herein, a method for manufacturing an electrolytic capacitor for an implantable cardioverter defibrillator is provided. The method includes forming an ester material by adding azelaic acid, boric acid, and ethylene glycol at between 120° C.-130° C. for 25-35 minutes to provide esterification, and cooling the ester material to between 55° C.-65° C. during a determined period between 25-35 minutes. The method also includes, adding at least one of ammonium hydroxide or anhydrous ammonia to the ester material after cooling the ester material, and adding a phosphoric acid to the ester material after adding the ammonium hydroxide to form an electrolytic material for the electrolytic capacitor.

Optionally, the cooling of the ester material to between 55° C.-65° C. during a determined period between 25-35 minutes includes quenching of the ester material. In one aspect, the ammonium hydroxide is not added to the azelaic acid, boric acid, and ethylene glycol when forming the ester material. In another aspect, adding the phosphoric acid to the ester material after adding the ammonium hydroxide increases the pH level of the electrolytic material to between 6.8 and 7.4.

DETAILED DESCRIPTION

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

All references, including publications, patent applications and patents, cited herein are hereby incorporated by reference to the same extent as if each reference were individually and specifically indicated to be incorporated by reference and were set forth in its entirety herein.

Terms

The term "ester material" when used herein describes any and all materials including organic compounds formed as a result of a chemical reaction between an alcohol and an acid resulting in a hydrogen of the acid being replaced with an alkyl or other organic group. The ester material may be formed from a single alcohol and single acid, multiple acids and a single alcohol, a single acid and multiple alcohols, or multiple acids and multiple alcohols. In one example, azelaic acid, boric acid, and ethylene glycol are the acids and alcohol utilized to form the ester material. The chemical reaction may result from a catalyst such as heat, temperature, energy, or the like.

The term "quenching" when used herein refers to the cooling of a material from a first higher temperature to a second lower temperate at a rate such that temperature processes, such as phase transformation, scintillation formation, etc. do not occur. In example embodiments, quenching can include cooling a material, such as an ester material, from a higher temperature of at least 130° C. to a lower temperature of at least 55° C. during a period of 30 minutes. In other examples, other temperature reductions and determined time periods can result in quenching. Such cooling can be accomplished by a chiller or a cooling coil apparatus.

The term "ammonium based material" when used herein includes any and all materials that include a nitrogen and at least three hydrogens bonded to one another. In one example, ammonium hydroxide (NH4OH) is an ammonium based material. In another example, anhydrous ammonia (NH3) is an ammonium based material.

The term "electrolytic material" when used herein includes any and all material utilized in making the electrically active part(s) or component(s) of an electrolytic capacitor.

The term "electrolytic capacitor" when used herein refers to any capacitor that is polarized and includes an anode or positive component, plate, layer etc. made from a metal to provide an insulating oxide layer through anodization that functions as a dielectric. An electrolyte covers, engages, interacts with the oxide layer to provide a negative component, plate, layer, etc. and functioning as a cathode. In one example, the electrolytic capacitor is an aluminum electrolytic capacitor that utilizes aluminum as the metal of the anode.

The term "scintillation rate" as used herein refers to a percentage of scintillations that occur in multiple electrolytic materials made from the same process. A scintillation is any defect, abnormality, etc. that occurs during manufacturing of an electrolytic material that results in damage to an oxide in use during an aging process to grow the oxide. As a result, the electrolytic material cannot be utilized for a capacitor. In one example, the scintillation causes the growth of oxide on the edges of a foil of a potential capacitor after stamping or laser cutting. The scintillation rate is measured by the total number electrolytic materials that cannot be utilized for forming an electrolytic capacitor compared to the total number of electrolytic materials made to be utilized for forming an electrolytic capacitor. In an example, if electrolytic material is utilized for forming 1000 electrolytic capacitors, and 4 electrolytic materials meant to be for forming the 1000 electrolytic capacitors are discarded resulting in the forming of 996 electrolytic capacitors, the scintillation rate is 0.4%. Similarly if 20 electrolytic materials are discarded and only 980 electrolytic capacitors are made the scintillation rate is 2%.

The term "deformation rate" as used herein refers to the rate at which charge time for an electrolytic material increases over time. In one example, an oxide from the electrolytic material causes a chemical reaction when no charge is presented in an electrolytic material, and in one example at 37° C. As a result, the amount of time for charging the electrolytic material over time increases as a result of the chemical reaction caused by the oxide. The deformation rate is a representation of this increased charge time, and in one example is calculated as a currently measured charge time minus an initial charge time divided by the initial charge time, times 100%:

(charge time measured−charge time initial)/(charge time initial)×100%

The charge time may be in units of seconds, millisecond, picoseconds, etc., and the deformation rate is expressed as a percentage.

The term "delivered to store ratio" and "DSR" as utilized interchangeably herein when utilized in relation to an electrolytic capacitor or an electrolytic material refers to the ratio of the amount of energy discharged from the electrolytic material or electrolytic capacitor to the amount of energy stored by that electrolytic material or electrolytic capacitor. In one example, the time period from delivering the energy to the electrolytic material to discharging the energy from the electrolytic material is between 10-15 milliseconds. During those 10-15 milliseconds energy is lost. For an ideal electrolytic material, the ratio would be 1, and the higher the ratio, the more efficient the electrolytic material. The ratio is unitless, as both the energy discharged, and energy stored contain the same units.

Embodiments may be implemented in connection with one or more implantable medical devices (IMDs). Non-limiting examples of IMDs include one or more of neurostimulator devices, implantable cardiac monitoring and/or therapy devices. For example, the IMD may represent a cardiac monitoring device, pacemaker, cardioverter, cardiac rhythm management device, implantable cardioverter defibrillator (ICD), neurostimulator, leadless monitoring device, leadless pacemaker, an external shocking device (e.g., an external wearable defibrillator), and the like. For example, the IMD may be a subcutaneous IMD that includes one or more structural and/or functional aspects of the device(s) described in U.S. application Ser. No. 15/973,195, titled "Subcutaneous Implantation Medical Device With Multiple Parasternal-Anterior Electrodes" and filed May 7, 2018; U.S. application Ser. No. 15/973,219, titled "Implantable Medical Systems And Methods Including Pulse Generators And Leads" filed May 7, 2018; U.S. application Ser. No. 15/973,249, titled "Single Site Implantation Methods For Medical Devices Having Multiple Leads", filed May 7, 2018, which are hereby incorporated by reference in their entireties. Additionally or alternatively, the IMD may include one or more structural and/or functional aspects of the device(s) described in U.S. Pat. No. 9,333,351 "Neurostimulation Method and System to Treat Apnea" and U.S. Pat. No. 9,044,710 "System and Methods for Providing A Distributed Virtual Stimulation Cathode for Use with an Implantable Neurostimulation System", which are hereby incorporated by reference. Further, one or more combinations of IMDs may be utilized from the above incorporated patents and applications in accordance with embodiments herein.

Additionally or alternatively, the IMD may include one or more structural and/or functional aspects of the device(s) described in U.S. Pat. No. 9,216,285 "Leadless Implantable Medical Device Having Removable and Fixed Components" and U.S. Pat. No. 8,831,747 "Leadless Neurostimulation Device and Method Including the Same", which are hereby incorporated by reference. Additionally or alternatively, the IMD may include one or more structural and/or functional aspects of the device(s) described in U.S. Pat. No. 8,391,980 "Method and System for Identifying a Potential Lead Failure in an Implantable Medical Device", U.S. Pat. No. 9,232,485 "System and Method for Selectively Communicating with an Implantable Medical Device", EP Application No. 0070404 "Defibrillator" and, U.S. Pat. No. 5,334,045 "Universal Cable Connector for Temporarily Connecting Implantable Leads and Implantable Medical Devices with a Non-Implantable System Analyzer", U.S. patent application Ser. No. 15/973,126, titled "Method And System For Second Pass Confirmation Of Detected Cardiac Arrhythmic Patterns"; U.S. patent application Ser. No. 15/973,351, Titled "Method And System To Detect R-Waves In Cardiac Arrhythmic Patterns"; U.S. patent application Ser. No. 15/973,307, titled "Method And System To Detect Post Ventricular Contractions In Cardiac Arrhythmic Patterns"; and U.S. patent application Ser. No. 16/399,813, titled "Method And System To Detect Noise In Cardiac Arrhythmic Patterns" which are hereby incorporated by reference.

Additionally or alternatively, the IMD may be a leadless cardiac monitor (ICM) that includes one or more structural and/or functional aspects of the device(s) described in U.S. patent application Ser. No. 15/084,373, filed Mar. 29, 2016, entitled, "Method and System to Discriminate Rhythm Patterns in Cardiac Activity"; U.S. patent application Ser. No. 15/973,126, titled "Method And System For Second Pass Confirmation Of Detected Cardiac Arrhythmic Patterns"; U.S. patent application Ser. No. 15/973,351, titled "Method And System To Detect R-Waves In Cardiac Arrhythmic Patterns"; U.S. patent application Ser. No. 15/973,307, titled "Method And System To Detect Post Ventricular Contractions In Cardiac Arrhythmic Patterns"; and U.S. patent application Ser. No. 16/399,813, titled "Method And System To Detect Noise In Cardiac Arrhythmic Patterns", which are expressly incorporated herein by reference.

Provided is an electrolytic capacitor that is manufactured using a controlled esterification process. During the esterification process, the time and temperature is monitored with a colorimetric analysis with conductivity, moisture content, and pH to produce a high voltage electrolytic material with minimal drop in DSR, and a reduced scintillation rate. Specifically, in forming the electrolytic capacitor, ethylene glycol, azelaic acid, and boric acid are heated together at 125° Celsius (° C.) for approximately thirty minutes to provide esterification. After the esterification, quenching occurs, and ammonium based materials such as ammonium hydroxide and anhydrous ammonia are then added. In particular, the ammonium hydroxide is not added during the esterification process, and not until after the quenching of the ester material to reduce chemical reactions between the ethylene glycol, azelaic acid, boric acid, and the ammonium based material. The final product yields a pH within 6.8 to 7.4, conductivity within 2.3 to 2.9 milli Siemens per centimeter (mS/cm) at between 29-31 deg Celsius (° C.), moisture content within 1.0 to 2.4%, phosphate concentration within 125 to 225 parts per million (ppm), and no visible color as determined by a colorimetric test (higher than 90% transmission). While DSR is reduced per the same conductivity, pH, and moisture content, such reduction is less than 1%. Meanwhile, the scintillation rate at higher voltages, such as at least 925 Volts significantly decreases. This is indicated by the aging rejects, or scintillation rate, dropping from greater than 6% to less than 0.5%. This process does allow for higher conductivity use to make up for the DSR if needed. Additionally, the new esterification process lowers the deformation rate by greater than 15% to allow for less battery life usage. Finally, the voltage withstand of the electrolyte is increased to handle higher voltages of up to 950 Volts with multiple continuous pulses above 300 times without failure. Specifically, a voltage withstand test, or hipot test, is run on electrical products such as capacitors by operating the product at a voltage much higher than the product would encounter in use.

Figure 1:
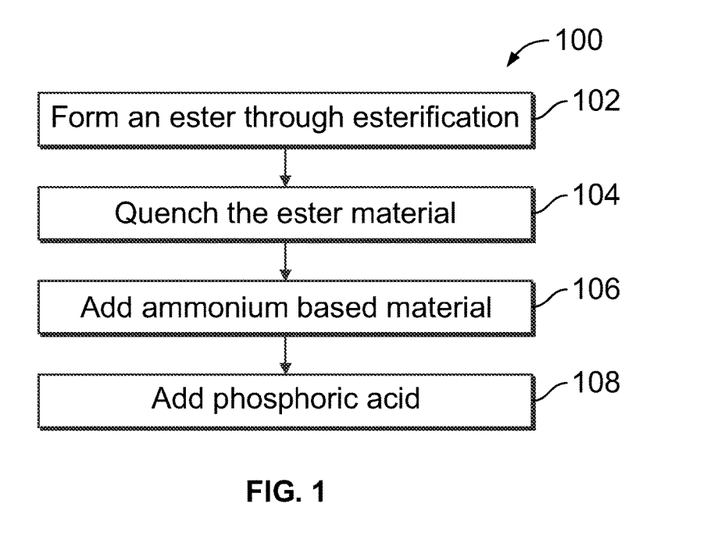
FIG. 1 illustrates a block flow diagram of a process of forming an electrolytic material in accordance with embodiments herein.

FIG. 1 illustrates a flow block diagram of a process 100 for forming an electrolytic capacitor. In one example, the electrolytic capacitor is an aluminum electrolytic capacitor. In another example, the electrolytic capacitor is formed for use in association with an IMD, and in particular an SICD. In yet another example a capacitor pair of the electrolytic capacitor formed from the process 100 includes electrical outputs for a 48 Joule, 925 Volt capacitor pair at about 8.4 cc volume.

At 102, esterification is provided between at least one acid and a glycol to form an ester material. In one example ethylene glycol, azelaic acid, and boric acid are added to one another and heated between 120° C.-130° C. for 25-35 minutes to provide the esterification. In one embodiment, the ethylene glycol, azelaic acid, and boric acid are added and heated to 125° C. for 30 minutes. Specifically, during esterification, an ammonium based material such as ammonium hydroxide is not added. While not adding the ammonium hydroxide during the esterification process reduces the DSR of the material per the same conductivity, pH, and moisture content, such reduction is minimal, such as 0.7%, or less than 1%. The moisture content represents the percentage of water in an electrolytic material by mass. Meanwhile, by not adding ammonium hydroxide during the esterification, the formation of scintillations in the material is reduced, minimizing aging rejects, or scintillation rate, from greater than 6% to less than 0.5%.

At 104, the ester material is quenched by rapid cooling. In one example, the ester material is cooled within 25-35 minutes, and in one embodiment 30 minutes, to between 55° C.-65° C., and in one embodiment 60° C. In one example, a chiller or cooling coil apparatus is utilized to provide the quenching of the ester material. By quenching the ester material after esterification and before additional materials, such as ammonium hydroxide, are added to the ester material, scintillation formation is reduced. Specifically, the energy required to form bonds between the ester material and ammonium hydroxide to incorporate the ammonium in the ester material that provides imperfections that are susceptible to scintillation is reduced, if not eliminated by bringing the temperature of the ester material down to the 55° C.-65° C. range before adding the ammonium hydroxide. As a result, the scintillation rate is significantly reduced.

At 106, an ammonium based material is added to the ester material, including to increase the pH of the ester material. In one example ammonium hydroxide, and anhydrous ammonia are added. The addition of the ammonium based material increase the pH of the ester material to including and between 6.8 to 7.4. Again, by waiting to add the ammonium hydroxide until after the heating step resulting in esterification, ammonium does not become part of the esterification process, reducing the formation of scintillations.

At 108, phosphoric acid is added to the ester material after adding the ammonium based materials to form the electrolytic material of the electrolytic capacitor. In one example, the phosphoric acid is added to yield 125 to 225 ppm phosphate. In this manner, the phosphoric acid represents an additional acid. Specifically, the phosphoric acid is considered an additional acid because the phosphoric acid is not added for the formation of the ester material itself such as in example embodiments where azelaic acid and boric acid are utilized in forming the ester material. Instead, the phosphoric acid is provided to introduce phosphate to the ester material after formation and quenching of the ester material. In this manner the phosphoric acid is an additional acid.

Table 1 below illustrates example volumes and mass of different

TABLE 1

| Ingredient Component | 1 L Volume (grams) | 4 L Volume (grams) | 12 L Volume (grams) |
| --- | --- | --- | --- |
| Ethylene Glycol | 905.1 to 906.9 | 3,620.4 to 3627.6 | 10,861.1 to 10,882.9 |
| Azelaic Acid | 59.9 to 60.1 | 239.7 to 240.3 | 719.3 to 720.7 |
| Boric Acid | 9.9 to 10.1 | 39.9 to 40.1 | 119.9 to 120.1 |
| Ammonium Hydroxide | 11.9 to 12.1 | 47.9 to 48.1 | 143.9 to 144.1 |
| Anhydrous Ammonia | Add to a pH of 6.8 to 7.4 | Add to a pH of 6.8 to 7.4 | Add to a pH of 6.8 to 7.4 |
| Phosphoric Acid | 0.21 to 0.23 | 0.87 to 0.89 | 2.63 to 2.65 |

The final product yields a pH within 6.8 to 7.4, conductivity within 2.3 to 2.9 mS/cm at between 29° C. to 31° C., moisture content within 1.0 to 2.4%, phosphate concentration within 125 to 225 ppm, and no visible color as determined by a colorimetric test (higher than 90% transmission). The phosphate concentration as used herein represents a percentage of the amount of phosphate in the electrolytic material as a measurement of mass compared to the total mass of the electrolytic material. Table 2 illustrates the performance of the electrolytic material when utilized as an electrolytic capacitor.

TABLE 2

| Conductivity (mS/cm) | CE2 (925 V)-SS Delivered Energy (V12%) | CE1 - Charge Time | CE1 (850 V) - Delivered Energy (V12%) | CE2 - SS Charge Time | CE2 (900 V)-SS Delivered Energy (V12%) | DSR |
| --- | --- | --- | --- | --- | --- | --- |
| 2.0 | 45.8 | 10.6 | 38.9 | 12.9 | 43.4 | 0.885 |
| 2.3 | 47.4 | 10.7 | 40.3 | 13.0 | 44.9 | 0.911 |
| 2.6 | 48.6 | 10.7 | 41.3 | 13.1 | 46 | 0.926 |
| 2.9 | 48.0 | 10.5 | 40.8 | 12.9 | 45.4 | 0.921 |

Specially, Table 2 shows the electrical outputs for a 48 J, 925 Volt capacitor pair at about 8.4 cc volume. The electrolyte material measured was formed utilizing the process 100 of FIG. 1. The only variance between electrolytic materials in the Table 2 is that during formation the conductivity was varied by either diluting with ethylene glycol to decrease conductivity, or added to the higher end of the chemical components to increase conductivity.

Figure 2:
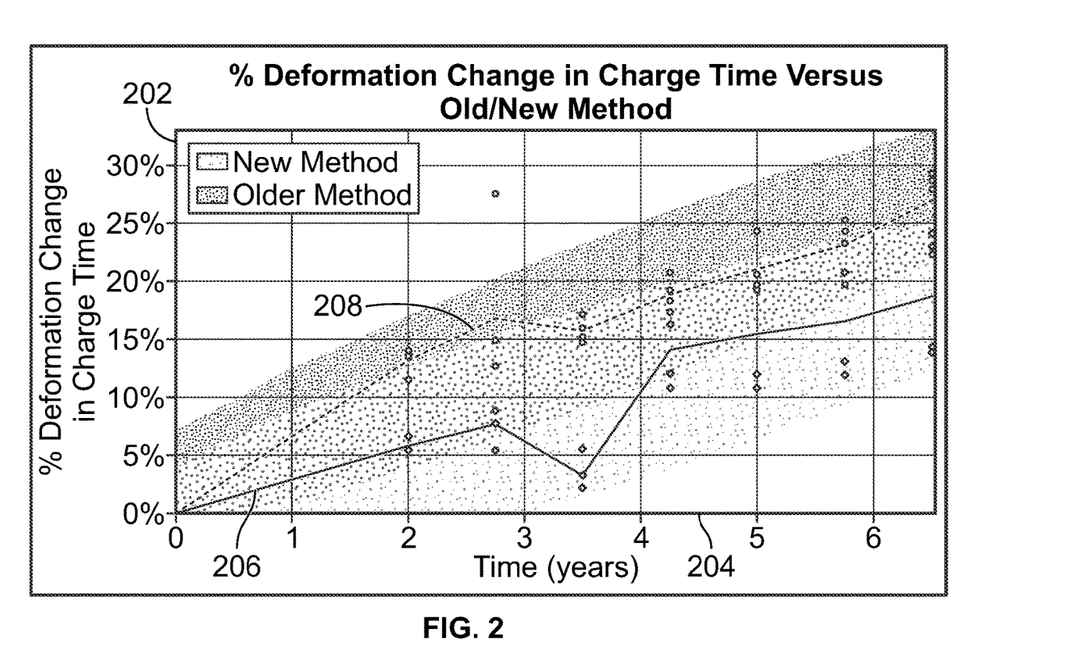
FIG. 2 illustrates a graph of average percent deformation change in charge time over time in accordance with embodiment herein.

FIG. 2 illustrates a graph of the electrolytic material made from the process 100 of FIG. 1 and presented in Table 2, compared to a process where ammonium hydroxide is added to the ester material during the esterification process. The graph illustrates the average percent deformation rate in charge time 202 over time 204 in years. Line 206 represents electrolytic materials made using the process 100 of FIG. 1, while line 208 represents electrolytic material made using a process where ammonium hydroxide is mixed with ethylene glycol, boric acid, and azelaic acid during the esterification process. The lines 206, 208 each represent an average of the deformation rates of numerous electrolytic materials tested.

As the graph shows, the electrolytic material has a less than 5% deformation rate after one year, as compared to an electrolytic material made when using ammonium hydroxide added during esterification. More specifically, the electrolytic material has a deformation rate of between 2%-5% after one year. After three and a half years, the deformation rate remained below 10% for the electrolytic material formed from the process of FIG. 1 while the deformation rate of the electrolytic material formed from a process adding ammonium hydroxide during esterification had a deformation rate over 15%. In addition, after six and a half years, the overall average deformation rate of the electrolytic material utilizing the method of FIG. 1 was decreased by more than 15% compared to a method wherein ammonium hydroxide is added during esterification. As a result, an unexpected increase in life is provided, preventing failures or reduced performance while providing similar electrical capabilities. Specifically, the electrolytic material formed from a process that includes ammonium hydroxide in the esterification process results in a DSR of approximately 0.926 at a conductivity of approximately 2.6 mS/cm. As indicated from Table 2, above or equal to 2.6 mS/cm the electrolytic material made from the process 100 of FIG. 1 were within less than 1% of such performance.

Figure 3:
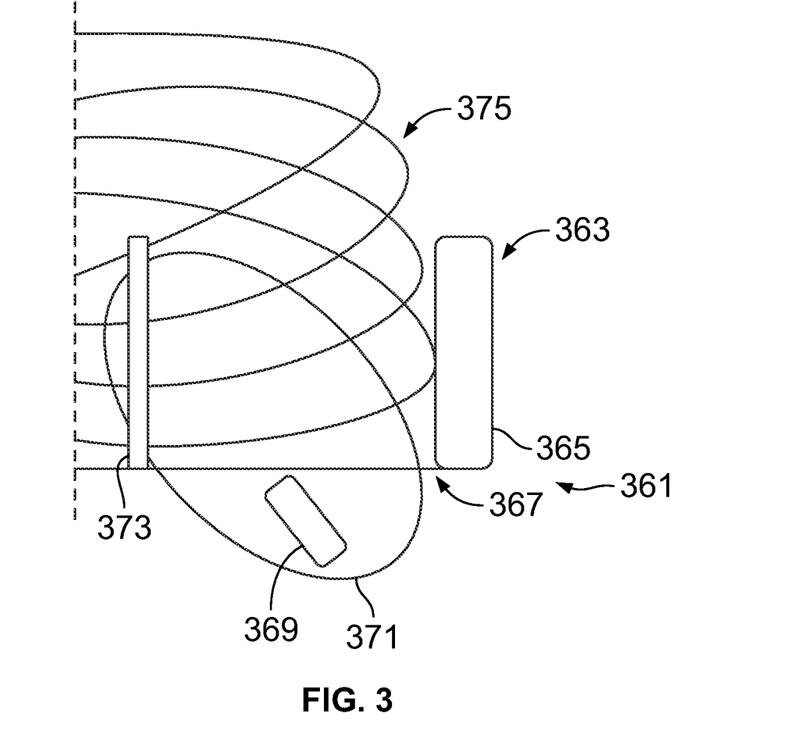
FIG. 3 illustrates of an IMD in accordance with embodiments herein.

FIG. 3 illustrates a schematic diagram of an implantable medical system 361 that is configured to apply VF therapy in accordance with embodiments herein. Embodiments may be implemented in connection with one or more subcutaneous implantable medical devices (S-IMDs). Non-limiting examples of S-IMDs include one or more of subcutaneous implantable cardioverter defibrillators (SICD). For example, the S-IMD may include one or more structural and/or functional aspects of the device(s) described in U.S. application Ser. No. 15/973,219, titled "IMPLANTABLE MEDICAL SYSTEMS AND METHODS INCLUDING PULSE GENERATORS AND LEADS", filed May 7, 2018; U.S. application Ser. No. 15/973,195, titled "SUBCUTANEOUS IMPLANTATION MEDICAL DEVICE WITH MULTIPLE PARASTERNAL-ANTERIOR ELECTRODES", filed May 7, 2018; which are hereby incorporated by reference in their entireties.

The system 361 includes a subcutaneous implantable medical device (S-IMD) 363 that is configured to be implanted in a subcutaneous area exterior to the heart. The S-IMD 363 is positioned in a subcutaneous area or region, and more particularly in a mid-axillary position along a portion of the rib cage 375. Optionally, the system 361 may also include a leadless pacemaker 369 implanted within the heart, such as at an apex 371 of the right ventricle. Optionally, the leadless pacemaker 369 may be omitted entirely. The system 361 does not require insertion of a transvenous lead.

The pulse generator 365 may be implanted subcutaneously and at least a portion of the lead 367 may be implanted subcutaneously. In particular embodiments, the S-IMD 363 is an entirely or fully subcutaneous S-IMD. Optionally, the S-IMD 363 may be positioned in a different subcutaneous region.

The S-IMD 363 includes a pulse generator 365 and at least one lead 367 that is operably coupled to the pulse generator 365. The lead 367 includes at least one electrode segment 373 that is used for providing MV shocks for defibrillation. In particular, an electrolytic capacitor manufactured utilizing the process of FIG. 1 can be utilized to provide the MV shocks. Optionally, the lead 367 may include one or more sensing electrodes. The pulse generator 365 includes a housing that forms or constitutes an electrode utilized to deliver MV shocks. The electrode associated with the housing of the pulse generator 365 is referred to as the "CAN" electrode.

In an alternative embodiment, the lead 367 may include one or more electrode segments, in which the electrode segments are spaced apart from one another having an electrical gap therebetween. The lead body may extend between the gap. One electrode segment may be positioned along an anterior of the chest, while another electrode segment may be positioned along a lateral and/or posterior region of the patient. The electrode segments may be portions of the same lead, or the electrode segments may be portions of different leads. The electrode segments may be positioned subcutaneously at a level that aligns with the heart of the patient for providing a sufficient amount of energy for defibrillation. The lead includes a lead body that extends from the mid-auxiliary position along an inter-costal area between ribs and oriented with the coil electrode(s) extending along the sternum (e.g., over the sternum or parasternally within one to three centimeters from the sternum). A proximal end the coil electrodes may be located proximate to the xiphoid process.

Figure 4:
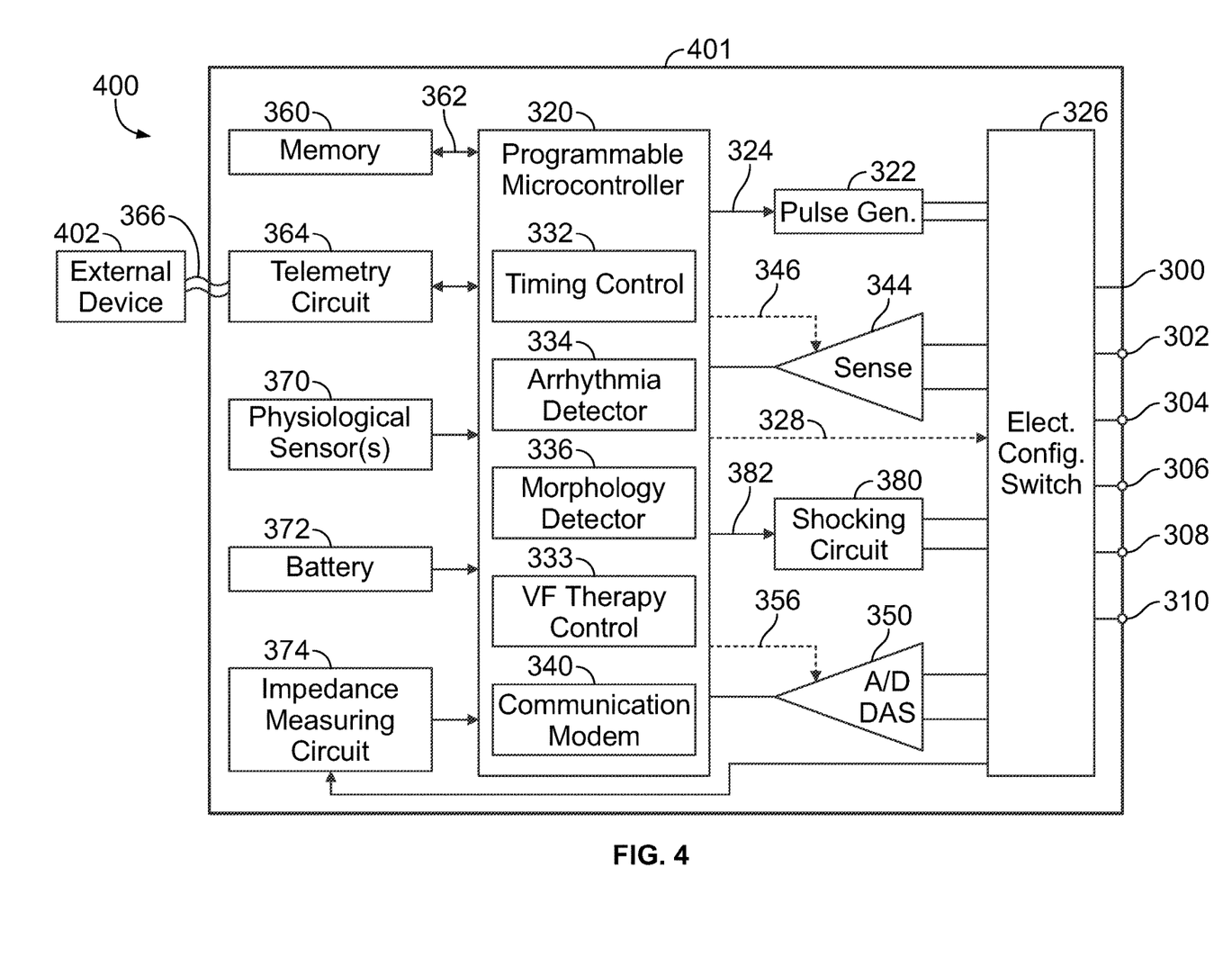
FIG. 4 illustrates a schematic block diagram of an IMD in accordance with embodiments herein.

FIG. 4 shows a block diagram of an exemplary S-IMD 400 that is configured to be implanted into the patient. The S-IMD 400 may treat both fast and slow arrhythmias with stimulation therapy, including cardioversion, pacing stimulation, an implantable cardioverter defibrillator, suspend tachycardia detection, tachyarrhythmia therapy, and/or the like.

The S-IMD 400 has a housing 401 to hold the electronic/computing components. The housing 401 (which is often referred to as the "can," "case," "encasing," or "case electrode") may be programmably selected to act as the return electrode for certain stimulus modes. The housing 401 further includes a connector (not shown) with a plurality of terminals 300-310. The terminals may be connected to electrodes that are located in various locations within and about the heart. The type and location of each electrode may vary. For example, the electrodes may include various combinations of ring, tip, coil, shocking electrodes, and the like.

The S-IMD 400 includes a programmable microcontroller 320 that controls various operations of the S-IMD 400, including cardiac monitoring and stimulation therapy. The microcontroller 320 includes a microprocessor (or equivalent control circuitry), one or more processors, RAM and/or ROM memory, logic and timing circuitry, state machine circuitry, and I/O circuitry. The S-IMD 400 further includes a ventricular pulse generator 322 that generates stimulation pulses for connecting the desired electrodes to the appropriate I/O circuits, thereby facilitating electrode programmability. The switch 326 is controlled by a control signal 328 from the microcontroller 320.

A pulse generator 322 is illustrated in FIG. 4. Optionally, the S-IMD 400 may include multiple pulse generators, similar to the pulse generator 322, where each pulse generator is coupled to one or more electrodes and controlled by the microcontroller 320 to deliver select stimulus pulse(s) to the corresponding one or more electrodes. The S-IMD 400 includes sensing circuit 344 selectively coupled to one or more electrodes that perform sensing operations, through the switch 326 to detect the presence of cardiac activity in the chamber of the heart 411. The output of the sensing circuit 344 is connected to the microcontroller 320 which, in turn, triggers, or inhibits the pulse generator 322 in response to the absence or presence of cardiac activity. The sensing circuit 344 receives a control signal 346 from the microcontroller 320 for purposes of controlling the gain, threshold, polarization charge removal circuitry (not shown), and the timing of any blocking circuitry (not shown) coupled to the inputs of the sensing circuit 344.

In the example of FIG. 4, the sensing circuit 344 is illustrated. Optionally, the S-IMD 400 may include multiple sensing circuits 344, where each sensing circuit is coupled to one or more electrodes and controlled by the microcontroller 320 to sense electrical activity detected at the corresponding one or more electrodes. The sensing circuit 344 may operate in a unipolar sensing configuration or a bipolar sensing configuration.

The S-IMD 400 further includes an analog-to-digital (A/D) data acquisition system (DAS) 350 coupled to one or more electrodes via the switch 326 to sample cardiac signals across any pair of desired electrodes. The A/D converter 350 is configured to acquire intracardiac electrogram signals, convert the raw analog data into digital data and store the digital data for later processing and/or telemetric transmission to an external device 402 (e.g., a programmer, local transceiver, or a diagnostic system analyzer). The A/D converter 350 is controlled by a control signal 356 from the microcontroller 320.

The switch 326 may be coupled to an LV lead having multiple LV electrodes, at least one of the LV electrodes configured to be located proximate to the LV site corresponding to the pacing site and to deliver the burst pacing therapy. The switch 326 may be further coupled to a second lead with at least one of a superior vena cava (SVC) coil electrode or an RV coil electrode, the shock vector including a CAN of the S-IMD and at least one of the SVC coil electrode or the RV coil electrode.

The microcontroller 320 is operably coupled to a memory 360 by a suitable data/address bus 362. The programmable operating parameters used by the microcontroller 320 are stored in the memory 360 and used to customize the operation of the S-IMD 400 to suit the needs of a particular patient. The operating parameters of the S-IMD 400 may be non-invasively programmed into the memory 360 through a telemetry circuit 364 in telemetric communication via communication link 366 (e.g., MICS, Bluetooth low energy, and/or the like) with the external device 402.

The S-IMD 400 can further include one or more physiological sensors 370. Such sensors are commonly referred to as "rate-responsive" sensors because they are typically used to adjust pacing stimulation rates according to the exercise state of the patient. However, the physiological sensor 370 may further be used to detect changes in cardiac output, changes in the physiological condition of the heart, or diurnal changes in activity (e.g., detecting sleep and wake states). Signals generated by the physiological sensors 370 are passed to the microcontroller 320 for analysis. While shown as being included within the S-IMD 400, the physiological sensor(s) 370 may be external to the S-IMD 400, yet still, be implanted within or carried by the patient. Examples of physiological sensors might include sensors that, for example, sense respiration rate, pH of blood, ventricular gradient, activity, position/posture, minute ventilation, and/or the like.

A battery 372 provides operating power to all of the components in the S-IMD 400. The battery 372 is capable of operating at low current drains for long periods of time, and is capable of providing a high-current pulses (for electrolytic capacitor charging) when the patient requires a shock pulse (e.g., in excess of 2 A, at voltages above 2 V, for periods of 10 seconds or more). In one example, the electrolytic capacitor that receives the high-current pulses is an electrolytic capacitor manufactured using the process of FIG. 1. In particular, the electrolytic capacitor can withstand higher voltages of up to 950 Volts with multiple continuous pulses above 300 times without failure. The battery 372 also desirably has a predictable discharge characteristic so that elective replacement time can be detected. As one example, the S-IMD 400 employs lithium/silver vanadium oxide batteries.

The S-IMD 400 further includes an impedance measuring circuit 374, which can be used for many things, including sensing respiration phase. The impedance measuring circuit 374 is coupled to the switch 326 so that any desired electrode and/or terminal may be used to measure impedance in connection with monitoring respiration phase. The S-IMD 400 is further equipped with a communication modem (modulator/demodulator) 340 to enable wireless communication with other devices, implanted devices and/or external devices. In one implementation, the communication modem 340 may use high frequency modulation of a signal transmitted between a pair of electrodes. As one example, the signals may be transmitted in a high frequency range of approximately 10-80 kHz, as such signals travel through the body tissue and fluids without stimulating the heart or being felt by the patient.

The microcontroller 320 further controls a shocking circuit 380 by way of a timing control 332. The shocking circuit 380 generates shocking pulses, such as MV shocks, LV shocks, etc., as controlled by the microcontroller 320. In accordance with some embodiments, the shocking circuit 380 includes a single change storage electrolytic capacitor that delivers entire phase I and phase II therapies. In one example, the electrolytic capacitor is manufactured utilizing the process of FIG. 1. The shocking circuit 380 is controlled by the microcontroller 320 by a control signal 382.

Although not shown, the microcontroller 320 may further include other dedicated circuitry and/or firmware/software components that assist in monitoring various conditions of the patient's heart and managing pacing therapies. The microcontroller 320 further includes a timing control 332, an arrhythmia detector 334, a morphology detector 336 and multi-phase VF therapy controller 333. The timing control 332 is used to control various timing parameters, such as stimulation pulses (e.g., pacing rate, atria-ventricular (AV) delay, atrial interconduction (A-A) delay, ventricular interconduction (V-V) delay, etc.) as well as to keep track of the timing of RR-intervals, refractory periods, blanking intervals, noise detection windows, evoked response windows, alert intervals, marker channel timing, and the like. The timing control 332 controls a timing for delivering the phase I, II and III therapies in a coordinated manner. The timing control 332 controls the phase II and III therapy timed relative to the MV shocks to cooperate with the MV shocks to terminate fibrillation waves of the ventricular arrhythmia episode and to reduce a defibrillation threshold of the heart below a shock-only defibrillation threshold.

The arrhythmia detector 334 is configured to apply one or more arrhythmia detection algorithms for detecting arrhythmia conditions. By way of example, the arrhythmia detector 334 may apply various VF detection algorithms. The arrhythmia detector 334 is configured to declare a ventricular fibrillation (VF) episode based on the cardiac events.

The therapy controller 333 is configured to perform the operations described herein. The therapy controller 333 is configured to identify a multi-phase VF therapy based on the ventricular fibrillation episode, the multi-phase VF therapy including MV shocks, LV shocks and a pacing therapy. The therapy controller 333 is configured to manage delivery of the burst pacing therapy at a pacing site in a coordinated manner after the MV and LV shocks. The pacing site is located at one of a left ventricular (LV) site or a right ventricular (RV) site. The therapy controller 333 is configured to manage delivery of the MV shock along a shocking vector between shocking electrodes.

The therapy controller 333 is further configured to analyze a timing of VF beats to obtain at least one of a VF cycle length (CL) or variation and to determine at least one of a number of pulses in a pulse train of the burst pacing therapy or a duration of pulse train of the burst pacing therapy based on at least one of the VF cycle length or variation. The therapy controller 333 may be further configured to set a timing delay to time the burst pacing therapy such that one or more of pulses therefrom occur during a period of time in which a local tissue region surrounding the pacing site is excitable and not refractory. The therapy controller 333 may be configured to set a frequency of the burst pacing therapy at a high frequency relative to a cycle length of non-fibrillation arrhythmias.

In accordance with embodiments, the S-IMD 400 may represent a subcutaneous implantable cardioverter defibrillator (SICD). Optionally, the communication modem 340 may be configured to wirelessly communicate with a leadless pacemaker, such as to pass timing information therebetween. The SICD may deliver phase I and II therapies, while the phase III pacing therapy may be delivered by the S-CID or the leadless pacemaker. The communication modem 340 may transmit timing information to a leadless pacemaker such as when sending an instruction for the leadless pacemaker to deliver pacing therapies in connection with embodiments herein. The communication modem 340 may receive timing information from a leadless pacemaker such as when receiving a direction from the leadless pacemaker that the low voltage therapy has been delivered or is currently being delivered and that SICD should now deliver the HV shock(s).

Closing

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A method for manufacturing an electrolytic capacitor for an implantable cardioverter defibrillator comprising:
   forming an ester material by adding at least one acid to a glycol;
   quenching the ester material for a determined period;
   adding an ammonium based material to the ester material after the ester material is quenched; and
   adding an additional acid after adding the ammonium based material to form an electrolytic material for the electrolytic capacitor.

2. The method of claim 1, wherein forming an ester material includes heating the at least one acid and glycol to between 120° C.-130° C. for 25-35 minutes to provide esterification.

3. The method of claim 1, wherein the at least one acid includes azelaic acid and boric acid, and the glycol is ethylene glycol.

4. The method of claim 1, wherein the ammonium based material is not added to the at least one acid and glycol when forming the ester material.

5. The method of claim 1, wherein the ammonium based material is at least one of ammonium hydroxide or anhydrous ammonia.

6. The method of claim 1, wherein the quenching the ester material includes cooling the ester material to between 55° C.-65° C. during the determined period.

7. The method of claim 6, wherein the determined period is between 25-35 minutes.

8. The method of claim 1 wherein the additional acid is phosphoric acid.

9. The method of claim 1, wherein the electrolytic material has a conductivity between 2.3 to 2.9 mS/cm at between 29° C. to 31° C. and a scintillation rate of between 0.4% and 2%.

10. The electrolytic capacitor of claim 9, wherein the electrolytic material has a pH in a range between 6.8 to 7.4.

11. The electrolytic capacitor of claim 10, wherein the electrolytic material has a moisture content in a range between 1.0-2.4%.

12. The electrolytic capacitor of claim 11, wherein the electrolytic material has a phosphate concentration in a range between 125 to 225 ppm.

13. The electrolytic capacitor of claim 9, wherein the electrolytic material has a deformation rate of between 2% and 5% after one year.

14. The electrolytic capacitor of claim 9, wherein the electrolytic material has a deformation rate of less than 20% after 6 years.

15. The electrolytic capacitor of claim 9, wherein the electrolytic material has a delivered to store ratio (DSR) of greater than 0.9.

16. The electrolytic capacitor of claim 9, wherein the electrolytic material has a delivered to store ratio of between 0.88 and 0.93.

17. A method for manufacturing an electrolytic capacitor for an implantable cardioverter defibrillator comprising:

forming an ester material by adding azelaic acid, boric acid, and ethylene glycol at between 120° C.-130° C. for 25-35 minutes to provide esterification;

quenching the ester material by cooling the ester material to between 55° C.-65° C. during a determined period between 25-35 minutes;

adding at least one of ammonium hydroxide or anhydrous ammonia to the ester material after cooling the ester material; and adding a phosphoric acid to the ester material after adding the ammonium hydroxide to form an electrolytic material for the electrolytic capacitor.

18. The method of claim 17 wherein the cooling of the ester material to between 55° C.-65° C. during a determined period between 25-35 minutes includes quenching of the ester material.

19. The method of claim 17, wherein the ammonium hydroxide is not added to the azelaic acid, boric acid, and ethylene glycol when forming the ester material.

20. The method of claim 17, wherein adding the phosphoric acid to the ester material after adding the ammonium hydroxide increases the pH level of the electrolytic material to between 6.8 and 7.4.

* * * * *